United States Patent [19]
Mundorf et al.

[11] Patent Number: 5,266,310
[45] Date of Patent: Nov. 30, 1993

[54] STABILIZATION OF THERAPEUTICALLY ACTIVE PROTEINS IN PHARMACEUTICAL PREPARATIONS

[75] Inventors: Traute Mundorf; Kurt Schnecker, both of Vienna, Austria

[73] Assignee: Boehringer Ingelheim International GmbH, Fed. Rep. of Germany

[21] Appl. No.: 661,346

[22] Filed: Feb. 28, 1991

Related U.S. Application Data

[63] Continuation-in-part of Ser. No. 243,743, Sep. 13, 1988, abandoned.

[30] Foreign Application Priority Data

Sep. 17, 1987 [DE] Fed. Rep. of Germany........ 3731255

[51] Int. Cl.$^5$ .................... A61K 37/02; A61K 37/36; A61K 37/48; A61K 37/66
[52] U.S. Cl. ................... 424/85.1; 424/85.4; 424/94.3; 424/484; 514/2; 514/12; 514/21; 514/944
[58] Field of Search ............ 424/85.1, 85.4, 85.5, 424/85.6, 85.7, 484, 498, 502, 94.3; 514/2, 12, 21, 944

[56] References Cited

U.S. PATENT DOCUMENTS

4,606,917  8/1986  Eppstein .................. 424/85

FOREIGN PATENT DOCUMENTS

| | | |
|---|---|---|
| 0080879 | 6/1983 | European Pat. Off. . |
| 0135171 | 3/1985 | European Pat. Off. . |
| 0152345 | 8/1985 | European Pat. Off. . |
| 0162332 | 11/1985 | European Pat. Off. . |
| 0177342 | 4/1986 | European Pat. Off. . |
| 0231816 | 8/1987 | European Pat. Off. . |
| 233629 | 8/1987 | European Pat. Off. . |
| 3240177 | 5/1983 | Fed. Rep. of Germany . |
| 61-277633 | 12/1986 | Japan . |
| 62-77333 | 4/1987 | Japan . |

OTHER PUBLICATIONS

Chemical Abstract 87:189297n.
Chemical Abstract 104:56428d (1986).

*Primary Examiner*—Jeffrey E. Russel
*Attorney, Agent, or Firm*—Sterne, Kessler, Goldstein & Fox

[57] ABSTRACT

This invention relates to pharmaceutical preparations for topical application containing one or more stabilized therapeutically active proteins and optional conventional excipients, carriers and additives, and a process for preparing pharmaceutical preparations of this kind and the use of physiologically acceptable hydrophobic substances for stabilizing proteins.

48 Claims, 3 Drawing Sheets

STABILIZATION OF THERAPEUTICALLY ACTIVE PROTEINS IN PHARMACEUTICAL PREPARATIONS

This application is a continuation-in-part of U.S. patent application Ser. No. 07/243,743, filed Sep. 13, 1988, now abandoned.

FIELD OF THE INVENTION

The invention relates to pharmaceutical preparations for topical application comprised of one or more stabilized, therapeutically active proteins and optional conventional excipients, carriers and additives. The invention also relates to a process for preparing these pharmaceutical preparations and the use of physiologically acceptable hydrophobic substances for the stabilization of proteins.

BACKGROUND OF THE INVENTION

One of the essential requirements in the topical application of therapeutically active proteins is their stability in the pharmaceutical formulation. The stability must be ensured for a sufficiently long period of time both during storage under refrigeration and at ambient temperature and also at body temperature, as well as "in situ" for several hours. Thus far, no entirely satisfactory solutions have been found to meet these requirements. Various substances for stabilizing interferons have already been proposed. For example, hydroxyethylcellulose has been used as a carrier substance for the preparation of gels or ointments containing interferon. However, under the conditions of use, there was some loss of activity of the interferons which could only be reduced by the addition of a protease inhibitor (EP-A-142345).

For the stabilizing of interferons in gels, ointments, etc., it has also been proposed to use various sugar alcohols, optionally together with sugar acids or the salts thereof, mild reducing agents, anionic surfactant or combinations of these substances (EP-A-80879).

For stabilizing proteins and polypeptides such as interferons, more particularly IFN-gamma, in parenteral preparations, it has been proposed to use a physically and chemically modified gelatin, particularly as a replacement for human serum albumin (EP-A-162332).

Japanese Published Patent Application JP-A-61-277633 discloses the stabilizing of interferons in solution with certain surface-active substances.

EP-A-135171 mentions human serum albumin as a suitable stabilizer for oil/water microemulsions.

For the topical application of the synergistic combination IFN-beta/9-(1,3-dihydroxy-2-propoxy-methyl-guanine (DHPG) in the form of an ointment, according to U.S. Pat. No. 4,606,917, albumin, dextrose and buffer substances are proposed as stabilizers.

A stabilizing effect to the standard required has not yet been achieved with the substances proposed thus far for stabilizing therapeutically active proteins, particularly in hydrogels.

The aim of this invention was to provide a stabilizer for therapeutically active proteins in pharmaceutical preparations for topical use, particularly in hydrogels, which in addition to being physiologically acceptable, satisfies all the requirements imposed on formulations of this kind, especially with respect to the optimum availability of the active substance and the full development of its activity and with respect to the gentlest possible method of preparation which takes account of the vulnerability of the proteins to shear forces.

Various substances have been investigated with respect to their suitability for solving the above-described problem. It was found, surprisingly, that even small amounts of hydrophobic substances used as additives in very finely divided form, particularly paraffin oils, have a stabilizing effect on various therapeutically active proteins which is superior to the effect of the substances proposed up till now. This result is all the more surprising as the pharmaceutical preparations for topical use which belong to the prior art, such as ointments in which hydrophobic substances are used as carriers in a suitably large proportion, require the separate addition of a stabilizer.

SUMMARY OF THE INVENTION

The invention relates to the use of physiologically acceptable hydrophobic substances, particularly paraffin oils, for stabilizing the therapeutically active proteins in pharmaceutical preparations for topical use, especially hydrogels. With the aid of the addition of a stabilizing quantity of hydrophobic substances in finely divided form, pharmaceutical preparations are obtained which, under the conditions of use, make the active substance available in active form over a lengthy period of time. By means of the pharmaceutical preparations according to the invention, the level of activity of the protein after a storage at 4°-8° C. over a period of at least 12 months is substantially unchanged. A further advantage of the formulations according to the invention is that there is less need to ensure that an exact pH value is maintained since the stabilizing addition of hydrophobic substances reduces the vulnerability of the proteins to fluctuations in the pH value. This advantage is of particular importance for applications which require lower pH values, e.g. application in the vaginal area.

The pharmaceutical preparation according to the invention also has the advantage, when present in the form of a hydrogel, of being extremely pleasant to use. This is because, even after the gel has dried, the presence of the hydrophobic substance ensures that the coating applied is soft to the touch, which is a particular advantage for application in the lip area.

The advantageous stabilizing effect of hydrophobic substances on proteins can possibly be put down to hydrophobic interactions which have hitherto been noticed scarcely or not at all. In the stabilizing of proteins according to the prior art, the following two operating principles were taken as a starting point: a) stabilizing by complex binding of the substance to the protein and hence steric fixing of the protein molecule; b) binding of the free bulk water by polar substances and hence stabilizing of the protein by influencing its hydrate coat. The hydrophobic interactions which presumably come into play in the present invention and which also occur in micellar structures occur around the time of stabilization by virtue of the fact that the hydrophobic regions of the protein which are created by the spatial distribution of the hydrophobic and hydrophilic amino acid groups are fixed to the oil/water phase interface so that the hydrophobic regions project into the oil droplet and the hydrophilic parts project into the polar phase.

BRIEF DESCRIPTION OF THE FIGURES

FIG. 1 shows that the addition of paraffin oil to the formulation disclosed in Example 1 ensures that the activity of IFN-gamma measured by the ELISA test (the antibodies used bind biologically active proteins for which they are specific) is maintained. The slight drop shown in the diagram is not significant in view of the test distribution.

FIG. 2 shows a comparison test with gelatine as a constituent of hydrogel formulation without the separate addition of a stabilizer.

FIG. 3 shows the stability curve over a period of 15 months for the hydrogel formulation described in Example 1.

FIG. 4 shows the stability curve for the hydrogel formulation described in Example 1.

FIG. 5 shows the curve of a comparison test in which the formulation described in Example 1 was used without any added paraffin oil. The results of the comparison test show a drop in stability shortly after manufacture.

FIG. 6 shows the stability curve for the formulation described in Example 11.

DESCRIPTION OF THE PREFERRED EMBODIMENTS

Figure 1:
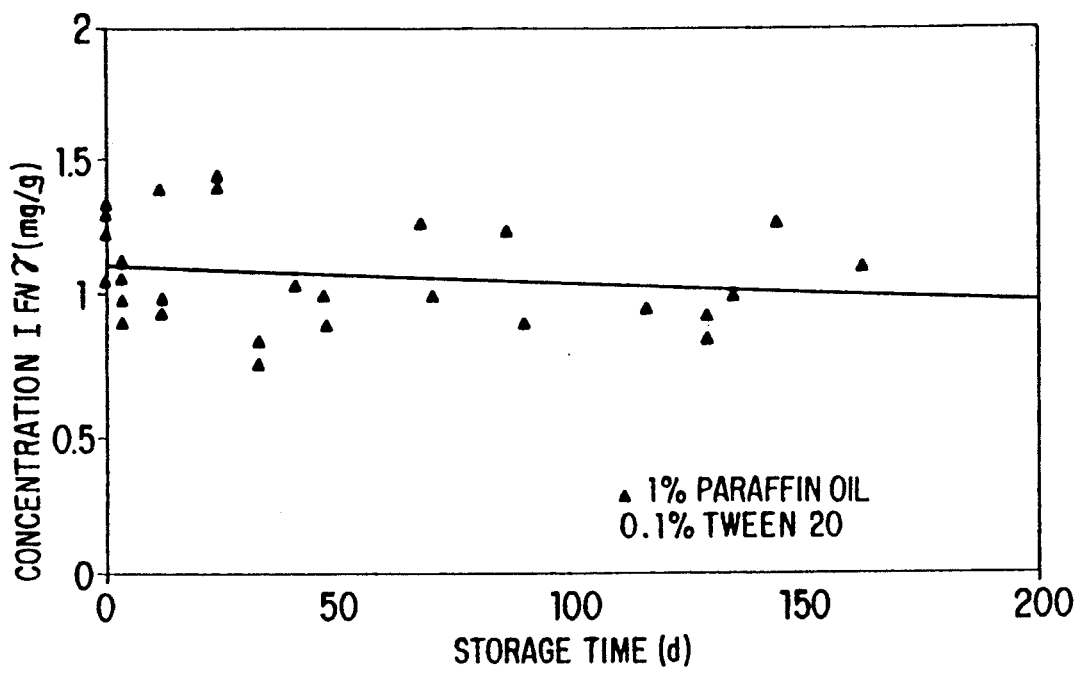
FIGS. 1-6 show the results of storage experiments with the various formulations described in the examples.

The invention thus relates to pharmaceutical preparations of the type mentioned above which are characterized in that they contain one or more physiologically acceptable hydrophobic substances, particularly paraffin oil or oils, in finely divided form in a quantity sufficient to stabilize the protein.

Suitable hydrophobic substances include, in addition to the preferred paraffin oils, higher fatty acids such as linoleic acid and palitic acid, or higher alcohols such as myristyl alcohol, or fatty acid esters such as triglycerides, or polyoxyethylenated and glycosylated glycerides (Labrafil ®), individually or in admixture. Of the paraffin oils, liquid, thin-liquid or thick-liquid paraffin oil according to Ph. Eur. and USP or mixtures thereof are suitable. The hydrophobic substances are preferably contained in the preparation in an amount of from 0.1% to 3.0%.

In order to ensure that the stabilizer is finely divided and the distribution is stable, emulsifiers may be added. The quantity used will depend particularly on the nature and quantity of stabilizer, the carrier used and, in the case of hydrogels, the viscosity thereof. In general, the quantity of the stabilizer is not more than 1%. Preferred emulsifiers include, in particular, non-ionic emulsifiers such as polysorbates (polyoxyethylene(n)-nonylphenylether), e.g. TritonR N101, TritonR N111, and poloxamer (polyethylenepolypropyleneglycol, PluronicR F68). If the pharmaceutical preparation is in the form of a hydrogel, the emulsifiers will not only bring about a fine distribution of the stabilizer but will also improve the spreading of the gels.

The pharmaceutical preparations according to the invention are suitable for the administration of human and animal proteins such as those listed as follows, including their structurally similar bioactive equivalents (by equivalents is meant those proteins which have substantially the same biological activity with a different amino acid sequence): cytokines, e.g. interferons such as huIFN-alpha, huIFN-beta, huIFN-gamma, huIFN-omega, hybrid interferons, animal interferons such as EqIFN-beta, EqIFN-gamma, or lymphokines such as interleukin-2, TFNbeta, or monokines such as interleukin-1, TNFalpha; growth factors, e.g. epidermal growth factor (EGF); anticoagulants, e.g. vascular anticoagulant proteins (e.g. VAC alpha, VAC beta), antithrombins; fibrinolytics, e.g. tPA, urokinase; proteins with an anti-allergic activity, e.g. IgE binding factor; therapeutically active enzymes, e.g. lysozyme, superoxide dismutases. The proteins used may either be of natural origin or produced by the recombinant method. A "functional derivative" of a protein is a compound which possesses a biological activity (either functional or structural) that is substantially similar to a biological activity of the protein. The terms "functional derivative" are intended to include the "fragments," "variants," "analogues," or "chemical derivatives" of the protein. The terms "functional derivative" are also intended to include glycoproteins corresponding to the protein which are present in animals, including humans. A "fragment" is meant to refer to any polypeptide subset of the protein molecule. A "variant" is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other or if the sequence of amino acid residues is not identical. An "analog" is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc. The moieties may alternatively decrease the toxicity of the molecule, eliminate or attenuate any undesirable side effect of the molecule, etc. Moieties capable of mediating such effects are disclosed in *Remington's Pharmaceutical Sciences* (1980). Procedures for coupling such moieties to a molecule are well known in the art. The range of indications depends on the biological activity of the protein which is to be applied; within the specific spectrum for each protein, any application is possible which requires topical administration of the active substance. The content of therapeutically active protein in the pharmaceutical preparation will naturally depend on the activity of the protein, the needs of the particular indication and the type of preparation used. It may span a wide range of quantities.

Suitable forms for administration include, in particular, hydrogels, suppositories and forms for vaginal use.

The use of excipients, carriers and additives will depend on the particular application selected, as care should be taken to ensure that they do not affect the stability of the protein by the type and quantity used. The carrier used will also depend on the form of administration; when the pharmaceutical preparation takes the form of a hydrogel, the carrier is water. Other excipients known in the art are fillers such as saccharides, for example, lactose or sucrose, mannitol or sorbitol cellulose preparations and/or calcium phosphates, for example, tricalcium phosphate or calcium hydrogen phosphate, as well as binders such as starch paste, using for example, maize starch, wheat starch, rice starch, potato starch, gelatin, tragacanth, methyl cellulose, hydroxypropylmethylcellulose, sodium carboxymethylcellulose, and/or polyvinyl pyrrolidone. In some cases, it may be desirable to add disintegrating agents such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. The preferred carrier for the present invention is water.

The pharmaceutical preparations according to the invention may contain, as additives, preservatives such as p-hydrobenzoates (nipa esters, methylparaben), sorbic acid, chlorhexidine digluconate, benzalkonium chloride and hexadecyltrimethyl ammonium bromide.

In order to accelerate the absorption of the active substance through the skin, permeation accelerators such as dimethylsulfoxide or tauroglycolic acid may be added to the pharmaceutical preparation.

Hydrogel forming agents which may be used include gelatine and cellulose derivatives such as methylcellulose, hydroxypropylcellulose and, in a particularly preferred embodiment, hydroxyethylcellulose, as well as synthetic polymers such as polyvinyl alcohol. The nature and quantity of the hydrogel forming agents used or the mixtures thereof will depend on the particular viscosity required. With regard to the fine distribution of the stabilizer, it should be noted that when the gel has a higher viscosity, the stability of the emulsion is, under certain circumstances, adequately ensured by the content of a hydrogel forming agent and therefore there is no need to add an emulsifier. The buffer systems used are selected according to the optimum pH for the particular protein and matched to the particular application; both organic and inorganic buffers may be used, e.g. succinate, acetate and phosphate buffers.

The additives which may be present also include moisture-retaining substances such as glycerol, sorbitol, 1,2-propyleneglycol, butyleneglycol and polyols.

The preparations in the form of hydrogels according to the invention are so-called "low-filled" emulsions, because of their low oil content, which tend to break down easily, as is well known. The preparation of these emulsions is, therefore, of particular importance with regard to their stability.

A two-step process is preferably used in the manufacture of the preparations according to the invention, particularly hydrogels.

In the first step, in a system of water/stabilizer/optionally emulsifier, a phase inversion from a W/O emulsion to an O/W emulsion is brought about and the fine pre-emulsion thus obtained is combined with the majority of the aqueous phase.

The following procedure is particularly preferred: first, a pre-emulsion is produced by the so-called "continental" method, the emulsifier is distributed in the paraffin oil and water is slowly added until a very coarse W/O emulsion is formed. At this stage, which is reached when the water content is about 20%-40%, according to our experiments, the mixing process is broken off and the emulsion is briefly allowed to settle. When mixing is subsequently resumed and water is added up to a content of about 50%, the emulsion is inverted to form a fine O/W emulsion. During the second step of the process, the pre-emulsion obtained is stirred into the buffer solution and dispersed, after which the hydrogel forming agent is added and allowed to swell. The time at which the protein solution is added is not critical; this is preferably the final step of the process. Using the preferred process according to the invention, extremely stable emulsions are obtained which show no tendency to separate after half a year's storage at room temperature.

In the case of smaller quantities or when technically more complicated homogenizers such as nozzle homogenizers are available, an O/W emulsion may also be produced in a single step without the preparation of a premulsion; however, the process which is preferred according to the invention provides a method of manufacture which not only produces a stable emulsion but is also simple, requires little energy or complex technology and is at the same time gentle.

The Examples which follow are intended to illustrate the invention with reference to hydrogel formulations containing IFN alpha, IFN gamma lysozyme, vac-a and TNF alpha as the therapeutically active protein:

EXAMPLE 1

100 grams of gel contain:

| | |
|---|---|
| IFN gamma | 0.2 g |
| Methylparaben | 0.2 g |
| Sodium dihydrogen phosphate monohydrate | 0.05 g |
| Dipotassium hydrogen phosphate trihydrate | 0.04 g |
| Natrosol 250 HX (hydroxyethylcellulose) | 1.75 g |
| Polysorbate 20 | 0.1 g |
| Thin-liquid paraffin oil | 1.0 g |
| Deionized water ad 100 g | 96.76 g |

The hydrogel was produced by the preferred two-step method:

a) Preparation of the Pre-emulsion

The phosphates and the preservative, methylparaben, were dissolved in hot water at 80° C., with stirring, and the solution was then cooled to ambient temperature. The emulsifier polysorbate 20 was distributed in the paraffin oil using a fast-rotating homogenizer. Sufficient water was added slowly, with stirring, to produce an approximately 30% coarse W/O emulsion. This emulsion was briefly left to stand, whereupon it separated. After the stirrer was switched on again the emulsion was brought to the point of phase inversion, to produce a very finely divided O/W emulsion.

b) Preparation of the Hydrogel

The paraffin oil emulsion was stirred into the sterile-filtered buffer solution and finely divided therein. Then microbiologically pure hydroxyethylcellulose was sprinkled into the emulsion and distributed therein with stirring. To obtain total swelling, the gel was left to swell for 10-15 hours under laminar flow. Finally, the IFN gamma solution, adjusted to 4 mg/ml, was slowly stirred in. This mixture was transferred into sterile tubes under laminar air flow conditions.

The course of the storage experiments is shown in FIG. 1. As can be seen from the diagram, the addition of paraffin oil ensures that the activity of IFN-gamma, measured by the ELISA test (the antibodies used bind biologically active proteins for which they are specific) is maintained; the slight drop shown in the diagram is not significant in view of the test distribution.

Figure 2:
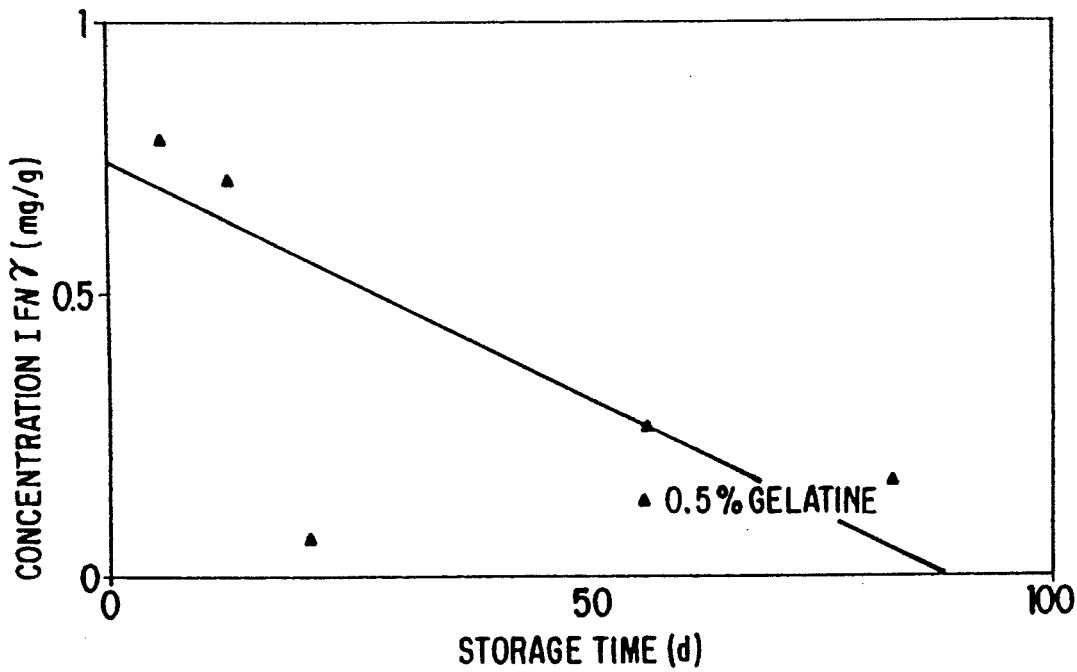

FIG. 2 shows a comparison test with gelatine as a constituent of a hydrogel formulation without the separate addition and showing the clearly destabilizing effect of gelatine on IFN-gamma. Consequently, when gelatine is used as a hydrogel forming agent, the addition of an effective stabilizer is absolutely essential.

Figure 3:
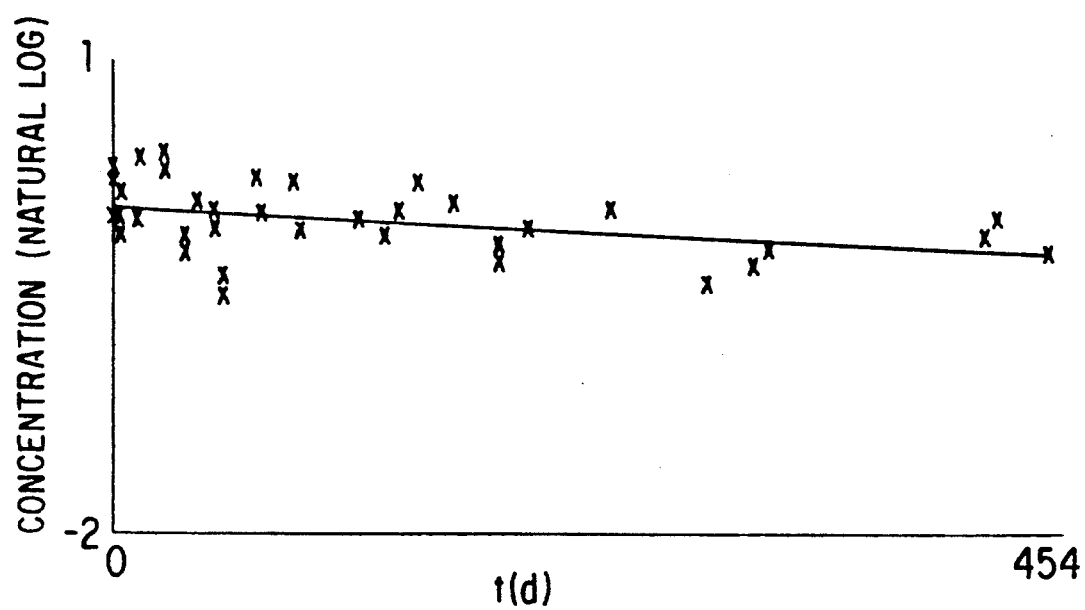
Figure 4:
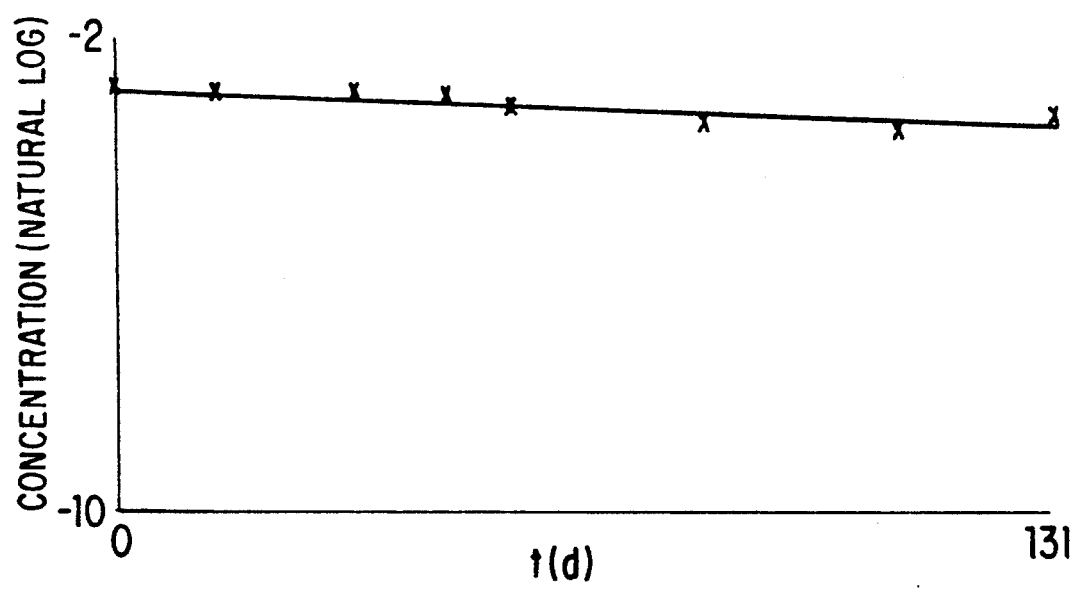
Figure 5:
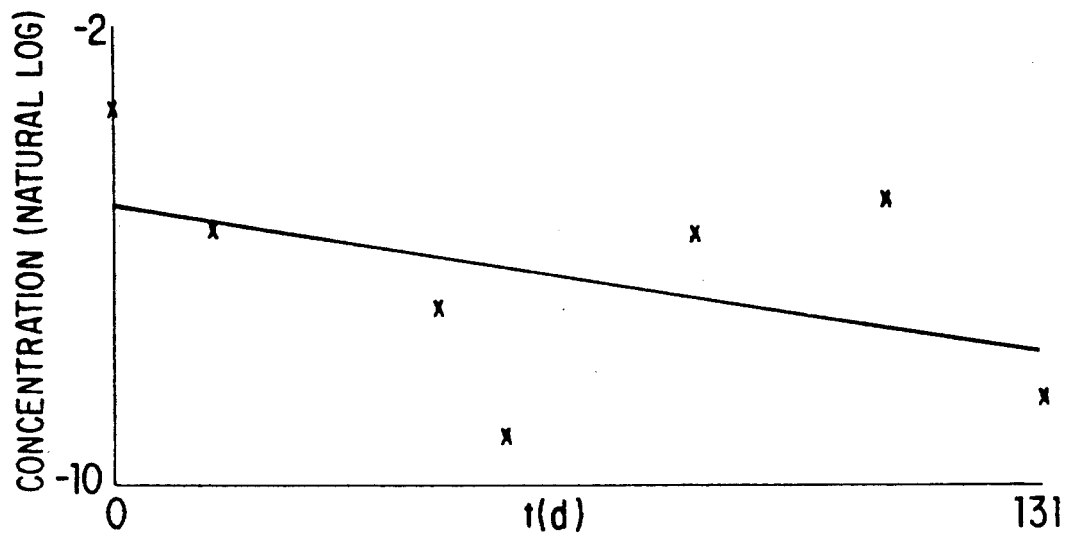
Figure 6:
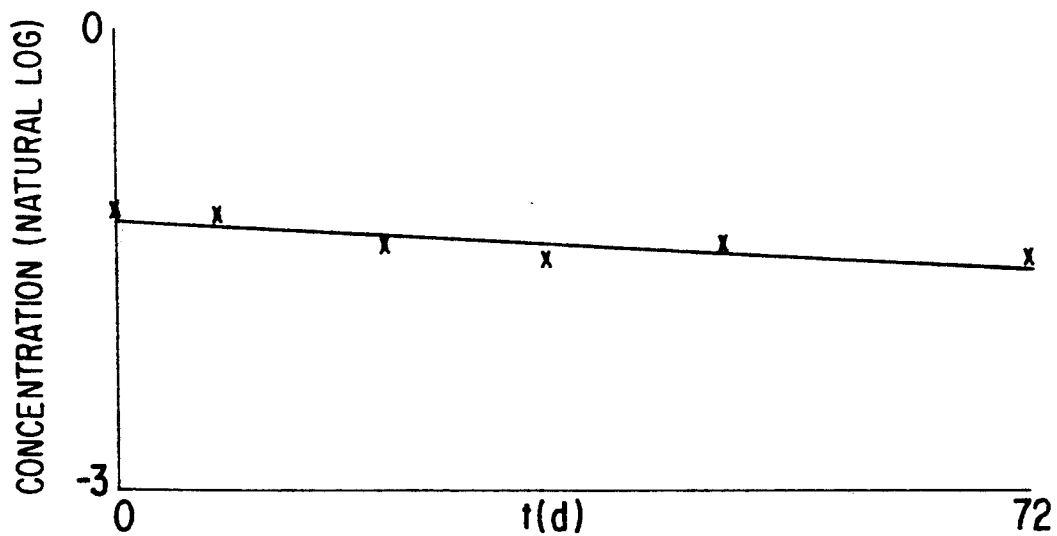

FIG. 3 shows the stability pattern over a period of 15 months (in this diagram and in FIGS. 4, 5 and 6, the log.nat. of the concentration of the therapeutically active protein is shown on the y axis).

EXAMPLE 2

100 g of gel contain:

| | |
|---|---|
| IFN gamma | 0.1 g |
| Methylparaben | 0.2 g |
| Sodium dihydrogen phosphate monohydrate | 0.05 g |
| Dipotassium hydrogen phosphate trihydrate | 0.04 g |
| Natrosol 250 HX | 1.75 g |
| Pluronic F68 | 0.1 g |
| Thin liquid paraffin oil | 1.0 g |
| Deionized water ad 100 g | 96.76 g |

The phosphates, the preservative methylparaben and the emulsifier Pluronic F68 were dissolved in hot water at 80° C. with stirring, and the solution was then cooled to ambient temperature and filtered to sterilize it. The paraffin oil was introduced and distributed therein by means of an homogenizer. Then the hydroxyethylcellulose was added with stirring in vacuo. Finally, the IFN-gamma solution, adjusted to 4 mg/ml, was added. The mixture was transferred as described in Example 1.

EXAMPLE 3

100 g of gel contain:

| | |
|---|---|
| TNF alpha | 0.1 g |
| Methylparaben | 0.213 g |
| Sodium dihydrogen phosphate monohydrate | 0.053 g |
| Dipotassium hydrogen phosphate trihydrate | 0.0427 g |
| Natrosol 250 HX | 1.87 g |
| Polysorbate 20 | 0.107 g |
| Thin liquid paraffin oil | 1.07 g |
| Deionized water ad 100 g | 96.5443 g |

The hydrogel was prepared as described in Example 1.

EXAMPLE 4

100 g of gel contain:

| | |
|---|---|
| IFN alpha | 0.0005 g |
| Methylparaben | 0.2 g |
| Sodium dihydrogen phosphate monohydrate | 0.05 g |
| Dipotassium hydrogen phosphate trihydrate | 0.04 g |
| Natrosol 250 HX | 1.75 g |
| Polysorbate 20 | 0.1 g |
| Thin liquid paraffin oil | 1.0 g |
| Deionized water ad 100 g | 96.8595 g |

The hydrogel was prepared as described in Example 1.

EXAMPLE 5

100 g of gel contain:

| | |
|---|---|
| IFN gamma | 0.100 g |
| Methylparaben | 0.2 g |
| Sodium dihydrogen phosphate monohydrate | 0.05 g |
| Dipotassium hydrogen phosphate trihydrate | 0.04 g |
| Tauroglycolic acid | 0.01 g |
| Natrosol 250 HX | 1.75 g |
| Polysorbate 20 | 0.1 g |
| Thin liquid paraffin oil | 1.0 g |
| Deionized water ad 100 g | 96.75 g |

The hydrogel was prepared as in Example 1 and tauroglycolic acid was stirred into the buffer solution as a permeation accelerator.

EXAMPLE 6

100 g of gel contain:

| | |
|---|---|
| IFN gamma | 0.05 g |
| Methylparaben | 0.2 g |
| Sodium dihydrogen phosphate monohydrate | 0.05 g |
| Dipotassium hydrogen phosphate trihydrate | 0.04 g |
| Natrosol 250 HX | 1.75 g |
| Polysorbate 20 | 0.1 g |
| Thin liquid paraffin oil | 0.6 g |
| Thick liquid paraffin oil | 0.4 g |
| Deionized water ad 100 g | 96.81 g |

The hydrogel was prepared as described in Example 1.

EXAMPLE 7

100 g of gel contain:

| | |
|---|---|
| IFN gamma | 0.05 g |
| Methylparaben | 0.2 g |
| Sodium dihydrogen phosphate monohydrate | 0.05 g |
| Disodium hydrogen phosphate trihydrate | 0.04 g |
| Natrosol 250 HX | 1.75 g |
| Myristyl alcohol | 1.0 g |
| Deionized water ad 100 g | 96.91 g |

The hydrogel was prepared as described in Example 2.

The myristyl alcohol was distributed in the sterile-filtered buffer solution which had been heated to about 60° C. After the buffer solution had cooled, the procedure was continued as described in Example 2.

EXAMPLE 8

100 g of gel substance contain:

| | |
|---|---|
| IFN gamma | 0.005 g |
| Methylpraben | 0.20 g |
| Succinate buffer pH 6.00 | 0.0191 M |
| Sodium chloride | 0.1435 M |
| Natrosol 250 HX | 1.75 g |
| Polysorbate 20 | 0.0952 g |
| Thin liquid paraffin oil | 0.952 g |
| Deionized water | ad 100 g |

The hydrogel was prepared as described in Example 1. The stability curve is shown in FIG. 4. FIG. 5 shows the curve of a comparison test in which the same formulation was used without any added paraffin oil. The results of the comparison test show a drop in stability shortly after manufacture.

EXAMPLE 9

100 g of gel substance contain:

| | |
|---|---|
| IFN gamma | 0.025 g |
| Methylparaben | 0.20 g |
| Succinate (buffer pH 6.2) | 0.2362 g |
| Sodium chloride | 0.8766 g |

-continued

| | |
|---|---|
| Natrosol 250 HX | 1.75 g |
| Polysorbate 20 | 0.1 g |
| LABRAFIL 1944 CS | 1.0 g |
| Deionized water | ad 100 g |

The hydrogel was prepared as described in Example 1.

EXAMPLE 10

100 g of gel substance contain:

| | |
|---|---|
| IFN gamma | 0.025 g |
| Methylparaben | 0.20 g |
| Succinate (buffer pH 6.2) | 0.2362 g |
| Sodium chloride | 0.8766 g |
| Natrosol 250 HX | 1.75 g |
| Polysorbate 20 | 0.1 g |
| LABRAFIL 2735 CS | 1.0 g |
| Deionized water | ad 100 g |

The hydrogel was prepared as described in Example 1.

EXAMPLE 11

100 g of gel substance contain:

| | |
|---|---|
| IFN gamma | 0.025 g |
| Methylparaben | 0.20 g |
| Succinate (buffer pH 6.2) | 0.2362 g |
| Sodium chloride | 0.90 g |
| Natrosol 250 HX | 1.75 g |
| Polysorbate 20 | 0.1 g |
| Myristyl alcohol | 1.0 g |
| Deionized water | ad 100 g |

The hydrogel was prepared as follows: the myristyl alcohol was melted at 50°-60° C. and then the premulsion was prepared as described in Example 1 but at 50°-60° C. The rest of the method was as in Example 1. The stability curve is shown in FIG. 6.

EXAMPLE 12

100 g of gel substance contain:

| | |
|---|---|
| TNF beta | 0.05 g |
| Methylparaben | 0.2 g |
| Sodium dihydrogen phosphate monohydrate | 0.05 g |
| Dipotassium hydrogen phosphate trihydrate | 0.04 g |
| Natrosol 250 HX | 1.75 g |
| Polysorbate 20 | 0.2 g |
| Thin liquid paraffin oil | 2.0 g |
| Deionized water | ad 100 g |

The hydrogel was prepared as described in Example 1.

EXAMPLE 13

| | |
|---|---|
| Lysozyme | 2.4 million units |
| Methylparaben | 0.2 g |
| Sodium dihydrogen phosphate monohydrate | 0.05 g |
| Dipotassium hydrogen phosphate trihydrate | 0.04 g |
| Natrosol 250 HX | 1.75 g |
| Polysorbate 20 | 0.2 g |
| Thin liquid paraffin oil | 2.0 g |
| Deionized water | ad 100 g |

The hydrogel was prepared as in Example 1.

EXAMPLE 14

100 g of gel substance contain:

| | |
|---|---|
| VAC alpha | 0.03 g |
| Methylparaben | 0.2 g |
| Sodium dihydrogen phosphate monohydrate | 0.05 g |
| Dipotassium hydrogen phosphate trihydrate | 0.04 g |
| Natrosol 250 HX | 1.75 g |
| Polysorbate 20 | 0.1 g |
| Thin liquid paraffin oil | 1.0 g |
| Deionized water | ad 100 g |

The hydrogel was prepared as in Example 1.

We claim:

1. A pharmaceutical composition obtainable by
   (a) mixing water, and at least one hydrophobic substance selected from the group consisting of paraffin oils, higher fatty acids, higher alcohols, and fatty acid esters and optionally an emulsifier to form a water/oil emulsion
   (b) inverting the water/oil emulsion to form an oil/water emulsion,
   (c) combining the oil/water emulsion obtained in step (b) with an aqueous solution to give an emulsion,
   (d) combining the emulsion obtained in step (c) with a hydrogel forming agent to form a hydrogel, and
   (e) adding at least one therapeutically active protein to the hydrogel,
   wherein the hydrophobic substance is mixed in an amount of from about 0.1% to 3.0% of the total weight of the final pharmaceutical composition.

2. The pharmaceutical composition of claim 1, wherein the aqueous solution in step (c) comprises a buffer.

3. The pharmaceutical composition of claim 2, wherein the buffer comprises at least one additive selected from the group consisting of permeation accelerators and moisture agents.

4. The pharmaceutical composition of claim 1, wherein said emulsifier is present in an amount of not more than 1% of the total weight of said pharmaceutical composition.

5. The pharmaceutical composition of claim 1, wherein said emulsifier is non-ionic.

6. The pharmaceutical composition of claim 5, wherein said emulsifier is a polysorbate.

7. The pharmaceutical composition of claim 1, wherein the water/oil emulsion has a water content of about 20% to 40% of the total weight of said water/oil emulsion.

8. The pharmaceutical composition of claim 1, wherein the oil/water emulsion has a water content of about 50% of the total weight of said water/oil emulsion.

9. The pharmaceutical composition of claim 1, wherein the higher fatty acid is linoleic acid or palmitic acid.

10. The pharmaceutical composition of claim 1, wherein the higher alcohol is myristyl alcohol.

11. The pharmaceutical composition of claim 1, wherein the fatty acid ester is a triglyceride, a polyoxyethylated glyceride, a glycosylated glyceride, or a mixture thereof.

12. The pharmaceutical composition of claim 1, wherein the therapeutically active protein is selected from the group consisting of cytokines, growth factors, fibrinolytics, anti-allergenics, lysozymes, and superoxide dismutases.

13. The pharmaceutical composition of claim 1, wherein said therapeutically active protein is selected from the group consisting of interferons, TNS-α, TNF-β, VAC-α and t-PA.

14. The pharmaceutical composition of claim 1, wherein said hydrogel forming agent is hydroxyethylcellulose.

15. The pharmaceutical composition of claim 1, wherein said hydrogel forming agent is a polyvinyl alcohol or gelatin.

16. The pharmaceutical composition of claim 1, further comprising a physiologically acceptable preservative.

17. The pharmaceutical composition of claim 16, wherein said physiologically acceptable preservative is selected from the group consisting of p-hydroxybenzoate, sorbic acid, chlorhexidine, digluconate, benzalkonium chloride, hexadecyltrimethyl ammonium bromide, and mixtures thereof.

18. A process for producing a pharmaceutical composition comprising one or more stabilized therapeutically active proteins comprising
   (a) mixing water, and at least one hydrophobic substance selected from the group consisting of paraffin oils, higher fatty acids, higher alcohols, and fatty acid esters, and optionally an emulsifier, to form a water/oil emulsion
   (b) inverting the water/oil emulsion to form an oil/water emulsion,
   (c) combining the oil/water emulsion with an aqueous solution to give an emulsion obtained in step (b),
   (d) combining the emulsion obtained in step (c) with a hydrogel forming agent to form a hydrogel, and
   (e) adding at least one therapeutically active protein to the hydrogel,
   wherein the hydrophobic substance is mixed in an amount of from about 0.1% to 3.0% of the total weight of said pharmaceutical composition.

19. The process of claim 18, wherein the aqueous solution in step (c) comprises a buffer.

20. The process of claim 19, wherein the buffer comprises at least one additive selected from the group consisting of permeation accelerators and moisture agents.

21. The process of claim 18, wherein the emulsifier is mixed in an amount of not more than 1% of the total weight of said pharmaceutical composition.

22. The process of claim 18, wherein said emulsifier is non-ionic.

23. The process of claim 22, wherein the emulsifier is a polysorbate.

24. The process of claim 18, wherein the water/oil emulsion has a water content of about 20% to 40% of the total weight of said water/oil emulsion.

25. The process of claim 18, wherein the oil/water emulsion has a water content of about 50% of the total weight of said oil/water emulsion.

26. The process of claim 18, wherein the higher fatty acid is linoleic acid or palmitic acid.

27. The process of claim 18, wherein the higher alcohol is myristyl alcohol.

28. The process of claim 18, wherein the fatty acid ester is a triglyceride, a polyoxyethylated glyceride, a glycosylated glyceride, or a mixture thereof.

29. The process of claim 18, wherein the therapeutically active protein is selected from the group consisting of cytokines, growth factors, fibrinolytics, anti-allergenics, lysozymes, and superoxide dismutases.

30. The process of claim 18, wherein said therapeutically active protein is selected from the group consisting of interferons, TNE-α, TNF-β, VAC-α and t-PA.

31. The process of claim 18, wherein said hydrogel forming agent is hydroxyethylcellulose.

32. The process of claim 18, wherein said hydrogel forming agent is a polyvinyl alcohol or gelatin.

33. The process of claim 18, further comprising the step of adding a physiologically acceptable preservative.

34. The process of claim 33, wherein said physiologically acceptable preservative is selected from the group consisting of p-hydroxybenzoate, sorbic acid, chlorhexidine, digluconate, benzalkonium chloride, hexadecyltrimethyl ammonium bromide, and mixtures thereof.

35. A topical pharmaceutical composition in the form of a hydrogel comprising
   (a) at least one therapeutically active protein,
   (b) a hydrophobic substance selected from the group consisting of paraffin oils, higher fatty acids, higher alcohols, and fatty acid esters in an amount of from about 0.1% to 3.0% of the total weight of said topical pharmaceutical composition,
   (c) a hydrogel forming agent, and
   (d) optionally, an emulsifier.

36. The topical pharmaceutical composition of claim 35, wherein the higher fatty acid is linoleic acid or palmitic acid.

37. The topical pharmaceutical composition of claim 35, wherein the higher alcohol is myristyl alcohol.

38. The topical pharmaceutical composition of claim 35, wherein the fatty acid ester is a triglyceride, a polyoxyethylated glyceride, a glycosylated glyceride, or a mixture thereof.

39. The topical pharmaceutical composition of claim 35, wherein said emulsifier is present in an amount of not more than 1% of the total weight of said topical pharmaceutical composition.

40. The topical pharmaceutical composition of claim 39, wherein said emulsifier is non-ionic.

41. The topical pharmaceutical composition of claim 40, wherein the emulsifier is a polysorbate.

42. The topical pharmaceutical composition of claim 35, wherein the therapeutically active protein is selected from the group consisting of cytokines, growth factors, fibrinolytics, anti-allergenics, lysozymes, and superoxide dismutases.

43. The topical pharmaceutical composition of claim 35, wherein said therapeutically active protein is selected from the group consisting of interferon, TNF-α, TNF-β, VAC-α and t-PA.

44. The topical pharmaceutical composition of claim 35, wherein said hydrogel is hydroxyethylcellulose.

45. The topical pharmaceutical composition of claim 35, wherein said hydrogel is a polyvinyl alcohol or gelatin.

46. The topical pharmaceutical composition of claim 35, further comprising a physiologically acceptable preservative.

47. The topical pharmaceutical composition of claim 46, wherein said physiologically acceptable preservative is selected from the group consisting of p-hydroxybenzoate, sorbic acid, chlorhexidine, digluconate, benzalkonium chloride, hexadecyltrimethyl ammonium bromide, and mixtures thereof.

48. The topical pharmaceutical composition of claim 35, further comprising at least one additive selected from the group consisting of a permeation accelerator, a moisture agent and a buffer.

* * * * *